(12) United States Patent
Zambrano Eder et al.

(10) Patent No.: US 10,400,224 B2
(45) Date of Patent: Sep. 3, 2019

(54) ENANTIOSELECTIVE MODIFIED ESTERASE ENZYME AND METHOD FOR THE PRODUCTION THEREOF

(71) Applicants: CORPORACIÓN CORPOGEN, Bogotá (CO); PONTIFICIA UNIVERSIDAD JAVERIANA, Bogotá (CO)

(72) Inventors: María Mercedes Zambrano Eder, Bogotá (CO); Sandra Baena Garzón, Bogotá (CO); Gina Pilar López Ramírez, Bogotá (CO)

(73) Assignees: CORPORACIÓN CORPOGEN, Bogotá (CO); PONTIFICA UNIVERSIDAD JAVERIANA, Bogotá (CO)

( * ) Notice: Subject to any disclaimer, the term of this patent is extended or adjusted under 35 U.S.C. 154(b) by 0 days.

(21) Appl. No.: 15/307,254

(22) PCT Filed: Apr. 30, 2015

(86) PCT No.: PCT/IB2015/000611
§ 371 (c)(1),
(2) Date: Jan. 9, 2017

(87) PCT Pub. No.: WO2015/166334
PCT Pub. Date: Nov. 5, 2015

(65) Prior Publication Data
US 2017/0130213 A1    May 11, 2017

(30) Foreign Application Priority Data
Apr. 30, 2014   (CO) .................................. 14-093195

(51) Int. Cl.
C12N 9/18    (2006.01)
C12P 41/00   (2006.01)
C12P 7/40    (2006.01)
C12N 15/55   (2006.01)
C12N 9/16    (2006.01)

(52) U.S. Cl.
CPC ................. *C12N 9/16* (2013.01); *C12N 9/18* (2013.01); *C12P 7/40* (2013.01); *C12P 41/005* (2013.01)

(58) Field of Classification Search
None
See application file for complete search history.

(56) References Cited

U.S. PATENT DOCUMENTS

2009/0221031 A1*   9/2009   Elend ....................... C12N 9/18
435/69.1

OTHER PUBLICATIONS

G. Lopez et al. "A novel thermoalkalostable esterase from *Acidicaldus* sp. strain USBA-GBX-499 with enantioselectivity isolated from an acidic hot springs of Colombian Andes", Applied Microbiology and Biotechnology, 98(20): 8603-8616 (Year: 2014).*

* cited by examiner

*Primary Examiner* — Rebecca E Prouty
(74) *Attorney, Agent, or Firm* — Birch, Stewart, Kolasch & Birch, LLP (57) ABSTRACT

This invention refers to the obtainment of a modified lipolytic enzyme that was isolated, expressed and purified from the heterologous expression. The gene sequence that codifies for the basal enzyme was obtained based on a thermo acidophilus organism of the acidobacteraceae family. This basal enzyme that comes from a thermo acidophilus organism, it is able to hydrolyze lipid substrates (triacylglycerols) united to middle chain fatty acids ($C_6$-$C_{10}$) such as tributyrine and tricapryln, among others. It also can carry out other inverse reactions to the hydrolysis such as synthesis reactions. On the other hand, this enzyme has enantioselective preference on (S) substrates of profens esters such as ibuprofen, naproxen and others. The enantioselective lipolytic basal enzyme was modified in its terminal C end to add an amino acid histidine tail that gives a higher efficiency in its purification process. The invention therefore refers to a method for making a pure, active polypeptide, which is called lipolytic enzyme 499EST obtained through the host *E. coli* BL 21 (DE3).

27 Claims, 3 Drawing Sheets
Specification includes a Sequence Listing.

SEQUENCE LISTING

<160> NUMBER OF SEQ ID NOS: 4

<210> SEQ ID NO 1
<211> LENGTH: 942
<212> TYPE: DNA
<213> ORGANISM: Acidicaldus sp.
<220> FEATURE:
<221> NAME/KEY: misc_feature
<223> OTHER INFORMATION: Nucleotide sequence of 499EST

<400> SEQUENCE: 1

```
atgccgcttg atcgccacgc cgaggccgtc ctcgagatga tccgccaatc gggacggccg      60
ccctatgaaa cgctcacccc ggccgaggcg cgcggcttgt accgccaggc gcgcgaggtg     120
ctcgccccgg agccgccgcc cgtggcagag gtgcgcgatc tctccctccc ccatcccgcc     180
gggcccgccc tacccacccg cctctaccgg ccgcagcagg gcggcgcgcc gcttcccctc     240
ctcgtctatt ccacggcgg gggctgggtg atcggcgatc tcgaaaccca tgacgtggtc     300
tgccgcgaga tcgccaaccg ggccggcatc ggcgtgctct ccatcgatta ccgcctcgcc     360
cctgagcaca aattccccgc cgccgtcgag gacgccttcg ccgcgacgcg ctgggcggcg     420
aaagaggccc caagcctcgg cttcgatccg gcccggctcg ccgtgggcgg ggacagcgcg     480
ggcggcaatc tcgctgccgt cgtctccctg ctcgcccgcg agcagggcgg cccgtcgatt     540
gcctttcagc tcctgatcta tcccgcgacc gatctcggca tgacccatcc ctcccatcag     600
cgctgggcag agggctatct cctcacccgc cccaccatgg agtggttccg cgcccattac     660
ctcaccgacc ccacccgcga gatcgccgat tggcgggtct ctccgctccg cgcccccgat     720
ctccgcggcc tgccgcccgc cttcgtgctg accgccgaat acgacccgct ggtcgatgag     780
ggcgaggact acgccgcccg cctcgccgcg gccggggtgc cggtcgcgac ccatcgcgtg     840
cccggcatga tccacggctt cctcaccatg ggcaaggcga tcccggcggc gaacgaggcg     900
ctcggcctca tcgccgaacg cctgcgcgca gcactcgcct ga                         942
```

<210> SEQ ID NO 2
<211> LENGTH: 313
<212> TYPE: PRT
<213> ORGANISM: Acidicaldus sp.
<220> FEATURE:
<221> NAME/KEY: misc_feature
<223> OTHER INFORMATION: amino acid sequence of 499EST

<400> SEQUENCE: 2

```
Met Pro Leu Asp Arg His Ala Glu Ala Val Leu Glu Met Ile Arg Gln
1               5                   10                  15

Ser Gly Arg Pro Pro Tyr Glu Thr Leu Thr Pro Ala Glu Ala Arg Gly
            20                  25                  30

Leu Tyr Arg Gln Ala Arg Glu Val Leu Ala Pro Glu Pro Pro Val
        35                  40                  45

Ala Glu Val Arg Asp Leu Ser Leu Pro His Pro Ala Gly Pro Ala Leu
    50                  55                  60
```

```
Pro Thr Arg Leu Tyr Arg Pro Gln Gln Gly Ala Pro Leu Pro Leu
 65                  70                  75                  80

Leu Val Tyr Phe His Gly Gly Gly Trp Val Ile Gly Asp Leu Glu Thr
                 85                  90                  95

His Asp Val Val Cys Arg Glu Ile Ala Asn Arg Ala Gly Ile Gly Val
            100                 105                 110

Leu Ser Ile Asp Tyr Arg Leu Ala Pro Glu His Lys Phe Pro Ala Ala
            115                 120                 125

Val Glu Asp Ala Phe Ala Thr Arg Trp Ala Lys Glu Ala Pro
130                 135                 140

Ser Leu Gly Phe Asp Pro Ala Arg Leu Ala Val Gly Gly Asp Ser Ala
145                 150                 155                 160

Gly Gly Asn Leu Ala Ala Val Val Ser Leu Leu Ala Arg Glu Gln Gly
                165                 170                 175

Gly Pro Ser Ile Ala Phe Gln Leu Leu Ile Tyr Pro Ala Thr Asp Leu
                180                 185                 190

Gly Met Thr His Pro Ser His Gln Arg Trp Ala Glu Gly Tyr Leu Leu
                195                 200                 205

Thr Arg Pro Thr Met Glu Trp Phe Arg Ala His Tyr Leu Thr Asp Pro
            210                 215                 220

Thr Arg Glu Ile Ala Asp Trp Arg Val Ser Pro Leu Arg Ala Pro Asp
225                 230                 235                 240

Leu Arg Gly Leu Pro Pro Ala Phe Val Leu Thr Ala Glu Tyr Asp Pro
                245                 250                 255

Leu Val Asp Glu Gly Glu Asp Tyr Ala Ala Arg Leu Ala Ala Ala Gly
                260                 265                 270

Val Pro Val Ala Thr His Arg Val Pro Gly Met Ile His Gly Phe Leu
                275                 280                 285

Thr Met Gly Lys Ala Ile Pro Ala Ala Asn Glu Ala Leu Gly Leu Ile
            290                 295                 300

Ala Glu Arg Leu Arg Ala Ala Leu Ala
305                 310

<210> SEQ ID NO 3
<211> LENGTH: 21
<212> TYPE: DNA
<213> ORGANISM: Escherichia coli
<220> FEATURE:
<221> NAME/KEY: misc_feature
<223> OTHER INFORMATION: initiator sequence

<400> SEQUENCE: 3
catatgccgc ttgatcgcca c                                              21

<210> SEQ ID NO 4
<211> LENGTH: 25
<212> TYPE: DNA
<213> ORGANISM: Escherichia coli
<220> FEATURE:
<221> NAME/KEY: misc_feature
<223> OTHER INFORMATION: initiator sequence

<400> SEQUENCE: 4
aagcttggcg agtgctgcgc gcagg                                          25
```

ENANTIOSELECTIVE MODIFIED ESTERASE ENZYME AND METHOD FOR THE PRODUCTION THEREOF

REFERENCE TO SEQUENCE LISTING SUBMITTED VIA EFS-WEB

This application includes an electronically submitted sequence listing in .txt format. The .txt file contains a sequence listing entitled "2017-01-09 SeqList 1556-0119PUS1.txt" created on Jan. 9, 2017 and is 4,967 bytes in size. The sequence listing contained in this .txt file is part of the specification and is hereby incorporated by reference herein in its entirety.

This invention was made by the Pontificia Universidad Javeriana and Corpogen, within the framework of the activities performed as part of the joint venture Centro Colombiano de Genómica and Bioinformatica de Ambientes Extremos-GEBIX, with the financing of Colciencias. In addition this invention is developed within the framework of genetic resources and derived products collected in an acid hotsprings of the National Natural Park of Los Nevados, that were accessed through the access contracts to genetic resources and derived products Number 15 of 2008, and number 76 of 2013, entered into by the Ministry of Environment and sustainable development and GEBIX.

SUMMARY—OBJECT AND PURPOSE OF THE INVENTION

This invention refers to the obtainment of a modified lipolytic enzyme that was isolated, expressed and purified from a heterologous expression. The gene sequence that encodes for the basal enzyme was obtained from a thermoacidophilus organism of the acidobacteraceae family. This basal enzyme that comes from a thermoacidophilus organism, is capable to hydrolyze lipid substrates (triacylglycerols) combined medium chain fatty acids ($C_6$-$C_{10}$) such as tributyrine, tricapryln, among others. It can also carry out other reactions inverse to hydrolysis, as synthesis reactions. On the other hand, this enzyme has enantioselective preference over (S) substrates of profens esters, such as ibuprofen, naproxen, among others.

The enantioselective basal lipolytic enzyme was modified in its C-terminal extreme to add an amino acids histidine tail that gives higher efficiency in its purification process. The invention therefore refers to a method to manufacture active pure polypeptide, which is called 499EST lipolytic enzyme obtained through the obtained through *E. Coli* BL21 host (DE3).

BACKGROUND INFORMATION

The finding of enzymes capable of catalyzing different reactions with high efficiency, stability and specificity can have origin from extremophile organisms, which are those that dwell in environment known as extreme. The enzymes of these organisms can have physical and chemical characteristics giving them generally stability to extreme conditions in which the organism that generates it lives.

The extremophile organisms as well as thermoacidophiles organisms can generate active enzymes in most cases, with low pH's and high temperatures. The acidophile organisms are known by the production of stable proteins such as proteases of *Sulfolobus acidocaldarius* (Fusek et. al. 1990), a-amylase of *Bacilus acidicola* (Serour & Satyanarayana, 2011), glucoamylases of *Picrophilus torridus* (Serour & Antranikian, 2002) and esterases of *Ferroplasma acidiphilum* (Golyshina et. al. 2006).

Hydrolytic enzymes esterases and lipases type have been described of thermoacidophiles mainly of the archaeans domain (Kim & Lee, 2004). Within the domain bacteria it is only known an esterase described from a thermoacidophile organism, *Alicyclobacillus acidocaldarius*, (Manco, et. al. 1998).

The importance of the lipolytic enzymes lies in their versatility when intervening in different catalytic processes, both of synthesis or hydrolysis of ester links, which can be applicable to different biotechnological processes. Among the properties of these enzymes are their high chemo, regio and enantio specificity. Biotechnologically, they can be useful in the synthesis of polymers, biodiesel, agrochemical products, flavoring compounds, hydrolysis of intermediate synthesis, or building blocks and besides in the resolution of racemic mixtures. (Hassanm, et al., 2006, Joseph et al. 2008

Due to its high degree of enantioselectivity, lipolytic enzymes are used in the resolution of racemic mixtures of compounds such as R/S-ibuprofen that belong to the family of the NSAIDs. Despite all the benefits, most of these medicaments have been commercialized as racemic mixtures mainly due to the high costs of separation of the enantiomers. The obtainment of enantiomers S-ibuprofen o S-naproxen show better benefits than the racemic mixture, for this reason it is important to find biological mechanisms of obtainment of simple enantiomers and this justifies the interest developed in recent decades for the obtainment of S (+)-2-pure aryl propionic acids. Now the transformation of the racemic mixture to obtain the S pure enantiomer is carried out through hydrolases, specifically lipolytic enzymes.

The Acidophilus thermo organism USBA-GBX-499 from which the basal esterase was obtained was isolated from an acid thermal spring from the National Natural Park of Los Nevados. This organism grows within a temperature range between 40° C. and 70° C. and a pH from 2.0 to 5.0 and degrades different substrata such as tributyrin, tricaprylin, ethyl oleate and others. From the extracellular fraction of the strain USBA-GBX-499 it was detected an enzymatic lipolytic activity from 0.01 U/mg. This low value indicated the presence of a thermostable lipolytic enzyme. Therefore, it was made the identification, clonation, expression and biochemical characterization of the thermo alkaline lipolytic enzyme called 499EST, which is modified in an intermediate stage of the purification process of the enzyme, thus obtaining the modified esterase enzyme which is the object of this invention.

Within the characterization of 499EST, it was identified an evaluation of enantioselectivity, its preference for the enantiomers (S)-ibuprofen and (S)-naproxen, which are enantiomers of high importance in the pharmaceutical industry.

DETAILED DESCRIPTION OF THE INVENTION

This invention will be described in a more complete manner, in relation with the figures that in the attached chapter show the main aspects conducive to carry out the invention.

The invention supplies a modified enzyme, which has lipolytic activity and is capable of implementing the racemic resolution of profens type enantiomers, among which are the ibuprofen S and R enantiomers, naproxen, among others.

The basal enzyme of the invention is characterized because it comes from a thermo acidophilus microorganism of the Acetobacteraceae family of the Alphaprofeobacteria class, which has demonstrated lipolytic activity in extreme culture conditions. In a preferred embodiment, the microorganism belongs to the *Acidicaldus* genre and in the most preferred embodiment the microorganism from which the enzyme comes is *Acidicaldus organivorans*, strain USBA-GBX-499.

Based on this microorganism, it was made the identification, cloning, expression and biochemical characterization of the lipolytic thermoalkakine enzyme called 499EST, which was modified in an intermediate stage of the purification process of the enzyme, where are added 5-10 residues of histidine in its C-terminal extreme, thus obtaining the modified enzyme which is the object of this invention.

The modified enzyme of the invention showed lipolytic activity at temperatures ranging from 35° C. to 75° C. and pH between 6.0 and 10.5 and more preferably at a temperature from 50° C. and 70° C. and pH between 8.0 and 10.0.

The modified enzyme of the invention acts surprisingly at intervals of alkaline pH as acidophilus organisms differently from the organism from which the wild enzyme comes, which grows at an acid pH as acidophilus organisms that belong to the Acetobacteraceae family. The modified enantioselective enzyme of the invention reaches an optimum activity at a temperature of 55° C. and a pH of 9.0.

Figure 3:
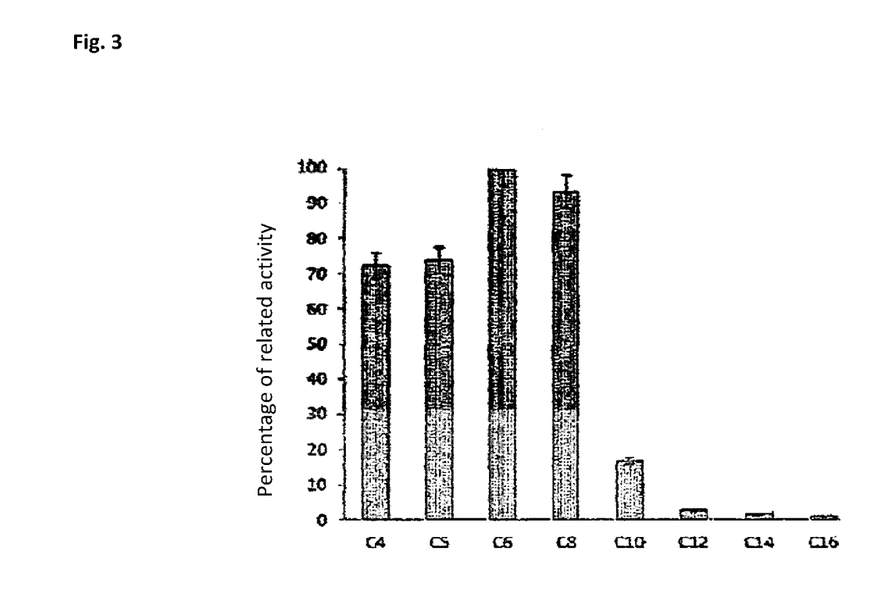
FIG. 3. Dependent activity of the substrate.

The modified enzyme of the invention hydrolyzes acyl chains from short to long ($C_2$-$C_{12}$), and in preferred embodiments it hydrolyzes those middle chain fatty acids ($C_6$-$C_{10}$) essentially p-nitrophenyl (pNP) caproate (FIG. 3). In a most preferred embodiment of the invention, the enantioselective enzyme also hydrolyzes triacylglycerols such as tributyrine and tricapryln.

Under these conditions, the enzyme showed an eniantoselective property allowing it to obtain from a racemic mixture a higher proportion of S type enantiomers. This activity of the enzyme implies an increase in the benefits of profens type medicaments or non-steroidal anti-inflammatory drugs due to the fact that in most cases the S enantiomer shows a positive effect, while the other, the R enantiomer has no effect or generates negative reactions.

Other characteristics of the enzyme invented are their stability in the presence of organic solvents and detergents, which can be used in the food industry to carry out synthesis processes to generate various esterified products.

The invented enzyme also includes, for example, a protein having an amino acid sequence with an identity of at least 75% to the amino acid sequence represented by SEQ ID No. 2, a histidine tail, and has enantioselective activity.

Figure 4:
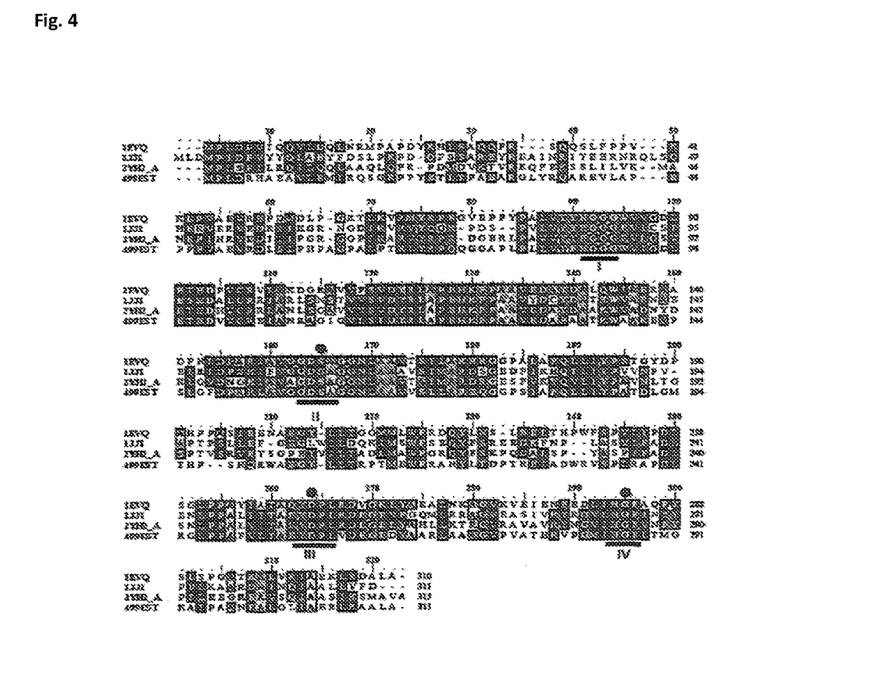
FIG. 4. Alignments between different esterases and the invented enzyme by identifying preserved blocks of sequences.

In FIG. 4, it can be seen the sites preserved and non preserved between the invented enzyme and the esterase of the invention belonging to the state of the art. The invented enzyme includes a protein having an amino acid sequence with identity of 75% or higher, 80% or higher, 85% or higher, 90% or higher, 95% or higher, 97% or higher, 98% or higher, 99% or higher, 99.5% or higher, 99.6% or higher, 99.7% or higher, 99.8% or higher, 99.9% or higher than the amino acid sequence represented by the SEQ ID No 2, and having the esterase activity.

An embodiment of the invention is the modified enzyme 499EST, which is encoded by a nucleic acid showing a nucleotide sequence, as described by the sequence SEQ ID No. 1, or with the amino acid sequence defined by the SEQ ID No 2 and a histidine tail from residues 5-10. Enzyme 499EST is encoded by a nucleic acid that shows a nucleotide sequence with an identity >75% with the SEQ ID No. 1 sequence and a 5' extreme modified with the addition of 5 to 10 HIs residues.

In a preferred embodiment of the invention, the 499EST enzyme comprises an amino acid sequence of >75% of identity according to the SEQ ID No. 2 and a sequence of 5-10 His residues in its C-terminal extreme.

In a particular embodiment, the modified 499EST enzyme increases its activity in presence of iron as $Fe^{+3}$ and $Mn^{2+}$, where the former favors up to 3 times more the specific activity of the enzyme when it is in a concentration from 2 to 10 mM.

In a particular embodiment of the invention, the modified enzyme 499EST that comes from an esterase of the organism *Acidicaldus organivorans* USBA-GBX-499, has an improved lipolytic activity and is capable to carry out the racemic resolution of profen type enantiomers, among which are the S and R enantiomers of ibuprofen and naproxen, (FIG. 2) among others.

This invention also supplies an ADN molecule that encodes the enantioselective enzyme of this invention. These sequences can also be inserted in an expression vector and be expressed in an adequate host, such as a prokaryotic *E. Coli* cell.

In a particular embodiment of the invention, it is obtained a host cell transformed by the modified gen of the esterase of the invention.

In a preferred embodiment, it is obtained a composition with the modified enzyme of 499EST of the invention, is highly stable in the presence of dimethyl sufoxide (DMSO) and glycerol reaching an increase in activity up to 100%, compared with the enzyme when in absence of the solvent.

Another embodiment of this invention corresponds to the method of obtainment of the esterase enzyme 499EST, that includes cloning, modification and purification.

Among the embodiments of the invention is included the use of the enantiomeric modified enzyme to generate profens enantiomers.

For the purpose of this invention, it is understood as "thermo acidophilus" an organism capable of growing optimally at temperatures higher than 50° C. and pH below 4.0.

For the purpose of this invention, it is understood as "acidophilus organisms" those organisms that grow optimally at pH lower than 4.0.

For the purpose of this invention, it is understood as "enzymes" those molecules generated by living organisms of proteic nature that catalyze or accelerate biochemical reactions.

The "lipolytic enzymes" comprise proteic molecules having catalytic activity on ester type links that can by hydrolyzed or synthesized. These enzymes belong to the family α/β hydrolases and are characterized by the plication generally composed by 8 β sheets connected by 6 helixes. Its activity is due mainly to the presence of a catalytic triad that is usually made of serine, histidine and asparagine (Ser-His-Asp). These are ubiquitous enzymes in nature and can be found under the denomination carboxylesterases, which according to certain characteristics can be classified as esterase or lipases.

For the purpose of this invention, it is understood as "lipase" the lipolytic enzyme called EC 3.1.1.3, which is characterized mainly for its capacity to cleave by hydrolysis or to synthesize ester links formed mainly by glycerol to fatty acids of long side chains, that is, higher than two carbon atoms.

For the purpose of this invention, it is understood as "esterase" the lipolytic enzyme called EC 3.1.1.1, which is characterized mainly the capacity to cleave or synthesize ester links that bind glycerol with short side chains, that is lower than ten carbon atoms.

In this manner, the expression "thermo alcalostable esterase" corresponds to enzymes in which the enzymatic activity is favored at temperatures higher than 50° C. and a pH>8.0 and is also not drastically affected throughout time by the effect of its exposure to this extreme environment.

For the purpose of this invention, it is understood as "enantioselectivity" the preferred embodiment of an enantiomer over two of its possible R or S versions. It can be partial, when the formation of one enantiomer is favored over the rest or it can be total, when it is only formed one enantiomer of the possible ones.

The term "enantiomer" is used to indicate that two isomers are non-superimposable mirror images. It is characterized for having an asymmetrical or chiral atom, being united to four different chemical groups.

"Racemic mixture" is understood as that solution in which the enantiomers are approximately in equivalent proportions. They are generally inactive mixtures.

For the purpose of this invention, it is understood as "lipolytic activity", the activity or process performed by the lipolytic enzymes through which they transform lipid substrates.

For the purpose of this invention, it is understood as "profens" or "aryl-2-propionic acids" those constituting a group of anti-inflammatory medicaments having as structural characteristic an asymmetric carbon allowing them to exist under the form of two enantiomers R-(–) and S-(+).

Enantiomers can differ widely in respect to their properties, as to benefits and disadvantages; generally the (S) enantiomers are active, while the (R) are inactive.

In this invention, "499EST" refers to the esterase enzyme modified, identified, cloned, expressed and purified, coming from the USBA-GBX-499 strain.

The modified enzyme 499EST of this invention corresponds to the esterase enzyme of SEQ No. 1 or SEQ No. 2 that shows a histidine tail at the C-terminal that corresponds between 5-10 histidine residues. Generally, a histidine tail containing n residues is represented in this document as His (n). The presence of a tail of histidine (or "His") helps to purify the enzyme.

In a preferred embodiment, the protein 499EST is expressed with a histidine tail from 5-10 and preferably six histidine residues. These residues are advantageous since they help with the purification.

The expression "host cell" is used to indicate a cell that contains a herologous gene that comprises SEQ No. 1 or equivalent and the His tail that encode for the modified enzyme of the invention, where this cell is preferably an *E. coli* prokaryotic cell.

In this invention, "a preservation agent" refers for example to a buffer. Preferably it is selected the buffer Tris-HCL at pH 9, even though other types of buffers and agents are within the scope of this invention.

The following particular embodiments of the invention allow construing the invention better and in no way are limited to the indicated developments.

EXAMPLE 1

Culture Conditions of the Strain and Obtainment of the Genomic DNA

The USBA-GBX-499 strain was cultured in 250 ml of the culture medium 991 at 55° C. at a pH of 3.0. The microbe culture, after 36 hours of cultivation, was centrifuged at 10000-a. 4° C. for 20 minutes. The collected cell pellet was washed several times with a solution of EDTA 100 mM and NaCl 0.8 M, pH 8.0. Afterwards, it was proceeded to the extraction of the genomic DNA. For this, it was resuspended the pellet in a lisis solution (487 μl of TE buffer, 40 μl of lisozime (20 mg/ml) and 20 μl of RNAsa (20 μg/ml). This mixture was incubated for a 1 hour period at 37° C. The further steps for the isolation of the genomic DNA were carried out as described by Diaz-Cárdenas et al., (2010).

EXAMPLE 2

Construction of the Genomic Library in Fosmids and Identification of Fosmids with Lipolytic Activity The library was constructed using the kit Copy Control™ Fosmid Library Production (Epicentre, USA) using the instructions of the commercial entity. The extracted DNA showed an average size from 30 to 40 kb. The extremes of the DNA were repaired to generate cohesive extremes, in order to link the DNA to the p CC1FOS vector. Thereafter, the DNA linked to the vector, was packed using MaxPlax Lambda Packaging Extract. The *E. coli* EP1300 was infected with the packed extracts following the protocol described by the supplier.

The *E. coli* EP cells, once transformed, were planted in LB medium supplemented with Chloramphenicol 12.5 μ/ml and incubated at 37° C. during 16 hours. Then were subcultivated the fosmids in liquid LB medium in plates of 96 wells, with volumes of 150 μg/ml and incubated under the same initial conditions. After finishing said period, it was added glycerol at 20% (v/v) and the fosmids were stored at −80° C. For the identification of the clones having positive lipolytic activity, the fosmids were sifted in a solid LB medium supplemented with tributyrin (TBT) at 1% (v/v).

Again, the fosmids that showed positive lipolytic activity were cultured in LB broth with Chloramphenicol 12.5 μg/ml and also with the self-inductor recommended by the commercial firm EPICENTER. After culturing all night, it was made the extraction of the fragment of DNA through an alkaline lisis, according to the protocol of Sambrook et al. 2001. The fragment was digested with different restriction enzymes, until obtaining fragments of DNA between 5 and 2.5 kb.

EXAMPLE 3

Subcloning and Sequence Analysis of the Esterase Gene

After having fragmented the DNA coming from the fosmid, were obtained fragments between 8 and 10 kb. These fragments were linked again to a vector that allowed obtaining clones that were again sifted in TBT, as it was explained in Example 2. When obtaining a positive clone, it was extracted the DNA fragment that encoded for the enzyme and this way were obtained between three and 5 kb. Again, the fragments were subcloned into a third vector Ptz19Rcm. It was sequenced completely a fragment of approximately 3 kb, through first walking using a ABI 3730XL DNA Analyser (Applied Biosystems) according to the supplier's instructions.

In this fragment, it was identified the complete sequence of the gene that encoded for the esterase.

With the identification of the sequence of nucleotids of the gene (SEC ID No. 1) that encodes for the basal enzyme, it was proceeded to identify the open reading frames (ORF, OPEN READING FRAME) by means of the ORF search tool of the NCBI. With the identification of the ORF's, it was obtained the sequence of amino acids of the basal protein (SEC ID No. 2)

EXAMPLE 4

Overexpression of the Gene and Purification of the Enzyme 499EST

After identifying and obtaining the complete sequence of the lipolytic gene, this is amplified by PCR using the initiators 5'-CATATGCCGCTTGATCGCCAC-3' (SEQ ID NO: 3) and 5'-AGCTTGGCGAGTGCTGCGCGCAGG-3' (SEQ ID NO: 4). The underlined portion indicates the cutting sites NdeI and Hind III, respectively. The products of PCR (pPCR) were obtained BY PCR touchdown. The Ppcr were purified and cloned in the vector pDrive in E. coli DH5α. Thereafter, for releasing the DNA fragment that encoded the enzyme, initially, the plasmid was extracted by alkaline lisis (Sambrook, et al., 2001) and then it was digested with the same restriction enzymes mentioned above. The released fragment was purified by means of QIAquick Gel Extraction Kit (QIA-GEN, Germany) according to the instructions of the commercial company.

Once the fragment was released, it was linked to the expression vector Pet21a(+) (Nowagen, Germany). This fragment is joined to a His Tag tail in the C-terminal region. This tail is acquired because the vector confers it. The location of the His Tag permits a correct plication of the molecule and therefore a bigger efficiency in its purification. The E. coli BL21 strain (DE3) was transformed with the DNA fragment, which is linked to the expression vector. The cells were cultured at 37° C. at 200 r.p.m. until reaching an optical density of 0.5 to 600. The induction of the production of recombining protein is performed with IPTG at a higher concentration of 0.05 mM and lower at 1 mM. The culture of E. coli BL21 (DE3) was incubated at a temperature higher than 20° C. and lower at 40° C., the agitation was maintained from 100 to 200 rpm. The induction was carried out for a period from 6 to 12 hours, period in which the cells were concentrated by a centrifugation of 8000 g for 15 minutes at 4° C. The pellet was frozen at −20° C. Thereafter, the pellet was re suspended in lisis buffer (50 mM $NaH_2PO_4$ with NaCl at a concentration higher than 50 mM and lower at 800 Mm, Triton X-100 0.01% (v/v), pH 8.0) with 1 mg/ml of lisozime.

Subsequently, the cells were disintegrated by ultrasonication. For removing thermolabile proteins, the disintegrated cells were incubated for 15 minutes within a temperature range from 50 and 70° C. The extract was centrifuged at 10000 g for 25 minutes at 4° C., the supernatant is decanted in a clean and sterile container. From this, charges of 1 ml were made in chromatographic separation columns by affinity at $Ni^{2+}$ prepacked Protino TED 2000©, every time that was added one ml of the sample, a wash of the column was made with the washing solution (50 mM $NaH_2PO_4$ with NaCl at a concentration higher than 50 mM and lower than 800 mM pH 8.0) besides Triton X-100 that was used in a concentration between 0.01% and 1% (v/v), pH 8.0. The use of NaCl and Triton X-100, helped to prevent hydrophobic interactions and therefore, non-specific unions of other proteins.

Once all the sample is charged in the column, from three to five washes were done with the washing solution in absence of NaCl and Triton X-100. The different washes permit to release from the column those proteins or residues of the lysed cells that had not been modified with the HisTag tail. Because the modified protein had the His Tag tail, it was generated a strong interaction between the protein and the $Ni^{2+}$ ions, which permitted its retention and further elusion with the eluting solution (50 mM $NaH_2PO_4$, 500 mM NaCl, and imidazole with a concentration between 100 and 250 mM, pH 8.0). Finally, the purified protein was recovered in a clean and sterile vial.

Thereafter, the product of the elution was concentrated in Amicon columns of 30 kDa. This concentration process was strictly necessary in order to be able to rule out the elution solution in which it was the protein and permit to leave it in a Tris-HCL buffer at a 9.0 pH, which permits stability to the modified protein. Under this condition, the protein can be stored for several months at 4° C. The purity of the protein was evaluated in a SDS-PAGE gel at 12% (p/v).

EXAMPLE 5

Enzyme Assays

The activity of the modified enzyme was determined spectrophotometrically at 405 nm in a range of temperatures between 45 and 75° C., using p-nitro phenyl of other chains C6 to C10 (Sigma-Aldrich) as substrate. One unit of esterase activity was defined as the capacity of the enzyme to release 1 μmol $min^{-1}$ of p-nitrophenol under the essay conditions. The molar absorbance coefficient was of 16.900 $M^{-1} cm^{-1}$. The mixture consisted of 448 μl of the Tris-HCl 50 mM buffer at 9.0 pH that contained 50 μl of p-nitrophenyl diluted in isopropanol and 2 μl of the solution stock of the protein. All the assays were made by triplicate and the average was calculated.

EXAMPLE 6

Specificity of the Substrate

The evaluated substrates were prepared in accordance with the protocol described by Ruiz (2005). The specificity of the substrate was evaluated by means of p-nitrophenyl ester of long and short chains (acetic acid ($C_2$), butanoic acid ($C_4$), pentanoic acid ($C_5$), hexanoic acid ($C_{10}$), hexadecanoic acid ($C_{16}$) and octodecanoic acid ($C_{18}$).

EXAMPLE 7

Optimum Temperature and pH

The optimum temperature of the modified enzyme was evaluated between 30 and 90° C. in buffer Tris HCl 50 mM (pH 9.0) exposing the enzyme to 30 minutes in each evaluated temperature (Suzuki et al., 2004, Park et al., 2006). The thermo stability essay was performed by incubating the enzyme at 55, 60 and 65 in Tris HCl 50 mM at pH between 7.5 and 10.0.

It was evaluated the activity of the enzyme by means of the p-nitrophenyl ester with some modifications, since for evaluating different pH values were used different buffer solutions, depending of the pH to evaluate: buffer acetate 50 mM (pH 5.0-6.0) buffer succinate (pH 4.0-5.5), MES (pH5.5-7.0). Tris HCl (pH 7.0-9.0) and sodium carbonate (pH 9.0-11.0) (Suzuki et. al., 2004, Park et. al. 2006). The protein was incubated for 15 minutes at a temperature higher than 45° C. and lower than 75° C. and then the quantification was made.

EXAMPLE 8

Effects of Metallic, Solvent, Detergents Ions and Inhibitors of the Enzyme

The evaluation of metallic, solvent and detergent ions and inhibitors of the modified enzyme was carried out incubating the enzyme in the presence of each of them for one hour at 30° C. The evaluation established the stability of the referenced enzyme at a control for which the enzyme was in absence of the additive. The result was expressed in percentage of residual activity, being 100% the control.

It was evaluated the effect of metallic ions on the enzyme activity. The ions evaluated were: $CaCl_2$, $FeCl_3$, $MgCl_2$, $CoCl_2$, $NiCl_2$, $ZnCl_2$, $CuCl_2$ and $MnCl_2$, the concentrations used were 1 mM and 10 mM. The effect of the ions $Fe^{3+}$ was evaluated at concentrations of 0.2 mM-10 mM, and its influence on the thermo stability between 50 and 65° C. (Table 1).

TABLE 1

Effect of metallic ions on the activity of the modified esterase 499EST. The activity was measured with pNPC8 at 55° C., pH 9.0 and defined as 100% in the essay of control without additives.

| Ion Metálico | Actividad relativa (%) | |
|---|---|---|
| | 1 mM | 10 mM |
| Control | 100 (±0.0) | 100 (±0.0) |
| $Ca^{2+}$ | 9 (±0.2) | 7 (±0.2) |
| $Fe^{3+}$ | 111 (±2.8) | 342 (±3.0) |
| $Mg^{2+}$ | 76 (±0.1) | 3 (±0.3) |
| $Co^{2+}$ | 74 (±7) | 23 (±2.9) |
| $Cu^{2+}$ | 16 (±2.5) | 0 |
| $Zn^{2+}$ | 190 (±10) | 21 (±3.1) |
| $Mn^{2+}$ | 252 (±5.5) | 127 (±4.0) |

The addition of 10 mM of $Ca^{+2}$, $Mg^{+2}$, $Co^{+2}$, $Cu^{+2}$ and $Zn^{+2}$ generates the highest enzyme inhibition (Table 1). However, 1 mM $Mm^{+2}$ caused an increase in the activity as well as the addition of $Zn^{+2}$ and the relative enzymatic activity in both cases was higher than 190%. On the other hand, in the case of $Fe^{+3}$ the enzymatic activity of 499EST was higher using a high concentration of $Fe^{+3}$ (10 mM) instead of a low concentration (1 mM).

The effect of the detergents, sodium dodecyl sulfate (SDS), Tween 20, Tween 80, Triton X-100, were evaluated at concentrations of 1 and 5% (v/v) (Table 2). In the evaluations it was determined the effect of inhibitors such phenylmethanesulfonyl fluoride-PMSF, ethylenediaminetetraacetic acid, EDTA, 2-mercaptoethanol (2-ME), dithiothreitol (DTT), the evaluated concentration was of 5 mM.

TABLE 2

The effect of detergents on the modified esterase 499EST. The activity was measured pNPC8 at 55° C., pH 9.0 as defined as 100% in the control assay without additives.

| Detergente | % actividad relativa | |
|---|---|---|
| | 1% | 5% |
| Control | 100 (±0.0) | 100 (±0.0) |
| SDS | 8 (±0.4) | 6 (±0.2) |
| Triton X-100 | 107 (±3.9) | 25 (±1.3) |
| Tween 80 | 85 (±3) | 32 (±1.3) |
| Tween 20 | 101 (±7.2) | 59 (±3.1) |

The evaluation of the activity of the modified enzyme 499EST with detergents (Table 2) showed that the enzyme was not affected by the addition of 1% of Triton X-100 and Tween 20. However, one higher concentration (5%), the activity decreased below 60%. On the contrary, the SDS strongly inhibits the lipolytic activity of 499EST The stability of 499EST was evaluated in the presence of each inhibitor; DTT was the only inhibitor that totally inhibits the enzymatic activity. When using EDTA and β-mercaptoethanol, the activity was inhibited, it was noticed a decrease in the relative enzymatic activity of 9 and 12% respectively. The inhibiting effect of the DTT and β-mercaptoethanol could be associated to the rupture of the disulfide bonds in the enzyme. The other inhibitors that interact with residues of Ser, such as PMSF, had inhibiting effect over the esterase and it was detected 80% of the activity.

Effect of organic solvents. The activity of the enzyme was evaluated in presence of different organic solvents. Two concentrations were evaluated, 15 and 30% of 1 butanol, 2 butanol, acetonitrile, acetone, 1-propanol, 2-propanol, methanol, ethanol, glycerol, dimethyl sulfoxide (DMSO), dimethyl formamide (DMF) (Table 3)

TABLE 3

Effect of organic solvents on modified esterase 489EST. The activity was measured with pNPC8 at 55° C., pH 9.0

| Solvente Orgánico | % actividad relativa | |
|---|---|---|
| | 15% | 30% |
| Control | 100 (±0.0) | 100 (±0.0) |
| 1-butanol | 1.5 (±0.01) | 0.0 |
| 2-butanol | 16.3 (±3) | 14.7 (±2.4) |
| Acetonitrilo | 17.0 (±0.5) | 0.0 |
| Acetona | 72.0 (±4) | 9.7 (±2.6) |
| 1-propanol | 26.8 (±1) | 24.81 (±2.4) |
| 2-propanol | 80.0 (±4) | 31.3 (±4.1) |
| Metanol | 3.0 (±0.5) | 0.0 |
| Etanol | 22 (±4) | 12.9 (±1.2) |
| DMSO | 180.0 (±8) | 200.2 (±12) |

TABLE 3-continued

Effect of organic solvents on modified esterase 489EST.
The activity was measured with pNPC8 at 55° C., pH 9.0

| Solvente Orgánico | % actividad relativa | |
|---|---|---|
| | 15% | 30% |
| DMF | 12.4 (±2) | 12.4 (±1.6) |
| Glicerol | 234.8 (±4.0) | 250.3 (±2.7) |

The activity of the modified enzyme 489EST was strongly inhibited by almost all the evaluated organic dissolvents (Table 3) except for DMSO and glycerol. The results showed that the enzyme was stable in the presence of both solvents at a concentration of 15% and 30%, in which, its esterase activity increased to 200 and 250%, respectively.

EXAMPLE 9

Evaluation of Enantioselectivity Through pNP Substrates

Enantioselectivity was evaluated through p-NP esters 2-methyl decanoic acid ibuprofen, and naproxen, which were determined by means of a spectrophotometric test in microplates of 96 wells. The reactions were carried out in the following manner:

i) 100 μl of the buffer Serensen 50 mM (pH 8.0) that contained sodium deoxycholate 5 Mm and acacia at 0.1% (v/v), were mixed with 15 μl DMSO, 5 μl of the stock solution of the 10 mM substrate, which was diluted in DMSO and 30 μl of the protein solution. The reaction was made at 64° C. The activity was determined by measuring absorbance at 410 nm at 30° C. It was calculated the p-Nitrophenol released by means of the calibration curve obtained by the absorbance of p-Nitrophenol at different concentrations.

Resolution of Racemic Mixtures of the Phenyl Ester Substrates of Ibuprofen, and Naproxen An evaluation was performed analytical scale to determine the kinetic resolution of phenyl ester substrates of ibuprofen and naproxen (Chow et al., 2012). The evaluation of the kinetic resolution for phenyl ester substrates of ibuprofen was developed in the following manner:

i) A solution with 17.32 Ml of buffer phosphate (100 mM, pH 8.0) was mixed with 2 ml. of DMSO and 0.66 mil of the stock solution of the substrate (10 mM in DMSO). To this solution it was added 100 μl of the enzyme to evaluate. The reaction was made with continuous agitation at a temperature from 45° C. and 75° C. for 80 minutes.

ii) The reaction was stopped by the addition of a concentrated solution of HCl (pH 1.0). Immediately thereafter, it was extracted the ibuprofen with methyl tertiary butyl ether (MTBE) twice with 20 ml of the solution.

iii) The ibuprofen was derivatized as a methyl ester after having added a solution of diazomethane 0.5 M in ethanol. The solvent was removed by means of reduction of pressure.

iv) The enantiomeric excess of the phenyl ester Ibuprofen and of the methyl ester ibuprofen was determined by means of chiral liquid high efficiency chromatography (HPLC—High performance liquid chromatography) (Dionex) using a Chiralpak IA column, under the following conditions:

A mobile phase n-heptane:isopropanol with a ratio of 99.8:0.2
A flow of 0.5 mL.min$^1$
Reading at 210 nm.

v) The retention time for the enantiomer (S) methyl ester ibuprofen was of 10:23 minutes, while that for the enantiomer (R) methyl ester ibuprofen was of 11:17 minutes. The retention time for the enantiomers (S) and (R) phenyl ester ibuprofen were of 16.32 and 18.07 respectively.

The enantioselectivity was evaluated by means of the kinetic resolution of the substrates phenyl ester naproxen and pNP ester naproxen. The procedure was the following (Chow et al., 2012):

i) 69.29 mL of a buffer phosphate solution (100 mM, pH 8.0) was mixed with 8 mL of DMSO-d6 and 2.64 mL of the stock solution of the substrate (10 mM in DMSO-d6). To this solution, it was added 200 μl of the enzyme to evaluate. The reaction was performed under continuous agitation at a temperature between 45° C. and 75° C. for 40 minutes.

ii) The reaction was stopped by adding a concentrated solution of HCl (pH 1.0). Immediately, the naproxen was extracted with MTBE twice with 20 ml of the solution.

iii) The extracted mixture of naproxen was dried under reduced pressure conditions. The transformation of this substrate was determined by means of MRI spectrographs (1H-NMR, Hydrogen-1 nuclear magnetic resonance) in which were compared the signals generated by the methyl groups from the naproxen and its corresponding esters.

iv) After measuring the samples containing the naproxen and the phenyl ester of naproxen, these samples were mixed with MTBE, 20 mL and extracted again with 20 mL, from an aqueous solution of NaHCO$_3$.

v) The aqueous phase was acidified with HCl and it was extracted with MTBE, 20 ml. The extracted naproxen was derivatized to methyl ester through the addition of a solution of diazomethane 0.5 M in ethanol. The solvent was removed by a reduced pressure.

vi) The enantiomeric excess of the methyl ester ibuprofen was determined by means of chiral liquid high efficiency chromatography (HPLC—High performance liquid chromatography) (Dionex) using a Chiralcel ODH, under the following conditions A mobile phase n-heptane: isopropanol with a ratio of 99:1
A flow of 0.5 mL.min$^1$
Reading at 225 nm.

vii) The retention time for the (S) and (R) enantiomers of methyl ester naproxen were of 22.84 and 19.39 minutes, respectively.

viii) The samples evaluated by NMR, underwent an additional test for determining the ee, by means of chiral HPLC with a CD detector (Jasco) using a Hyperclone ODS C18 column, under the following conditions:

A mobile phase of acetonitrile:water in a ratio of 80:20.
Flow of 0.5 mL.min$^{-1}$
Reading of 220 nm ix) The retention time for the p-NP ester of naproxen was of 3.83 minutes. The CD signal was measured at 280 nm.

Figure 1:
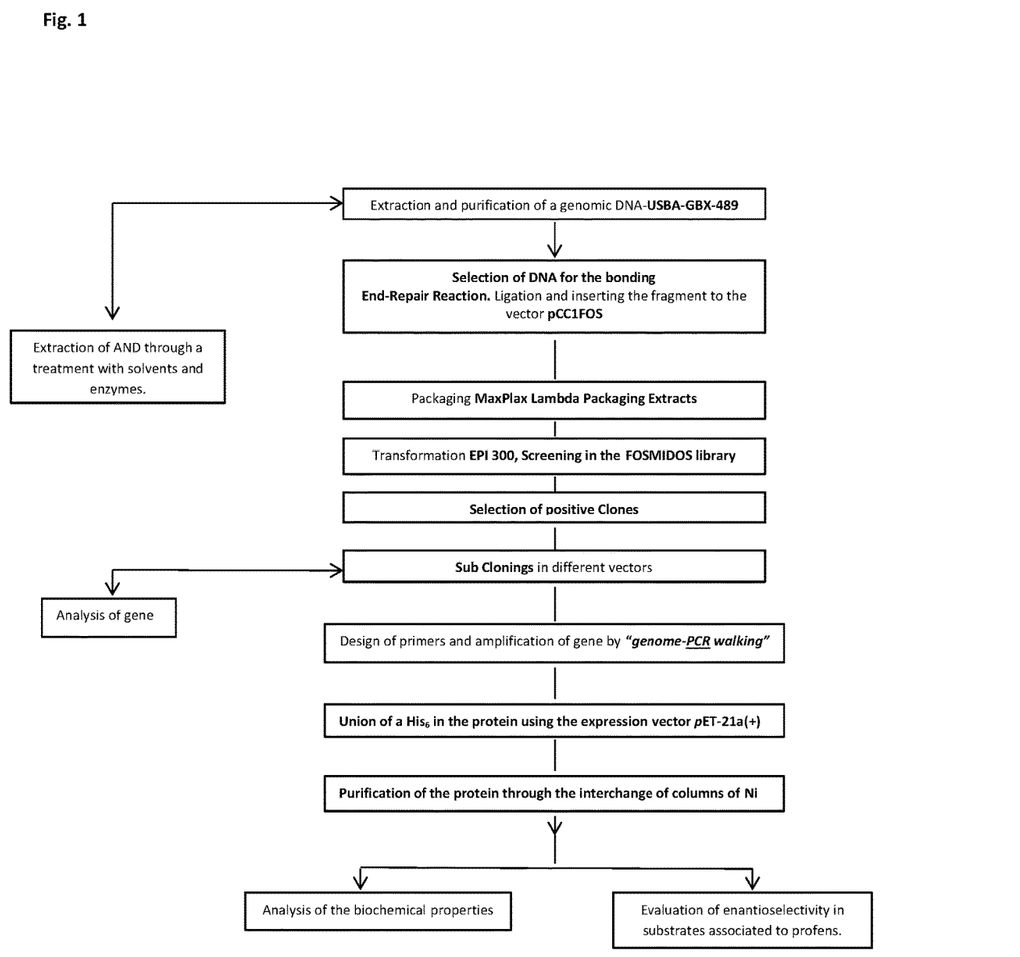
FIG. 1. Process of obtainment of the purified enzyme
Figure 2:
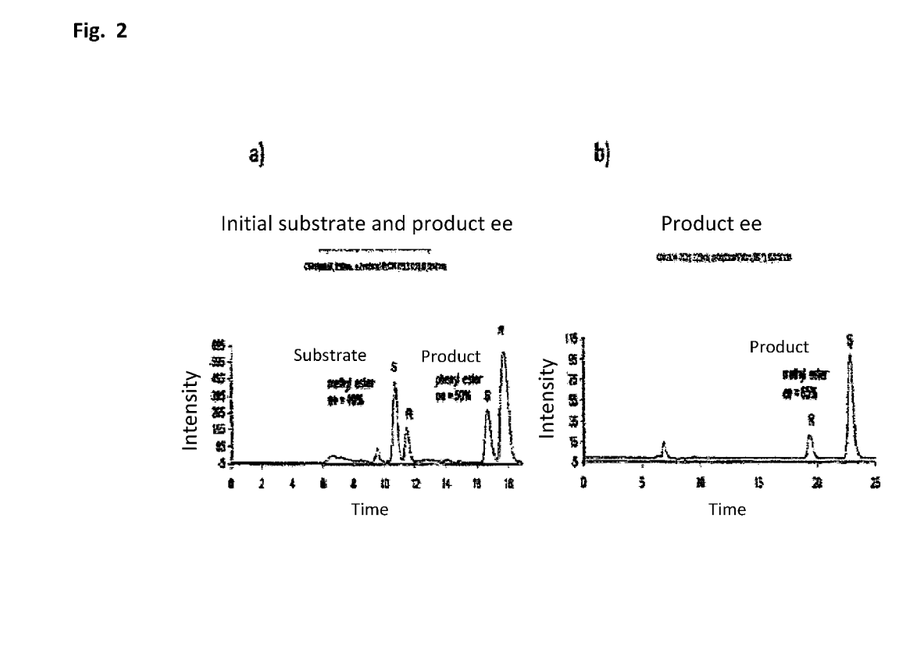
FIG. 2. Distribution of methyl ester and phenyl ester of ibuprofen (a) and methyl ester of naproxen (b) in an enantioselective manner.
Figure 5:
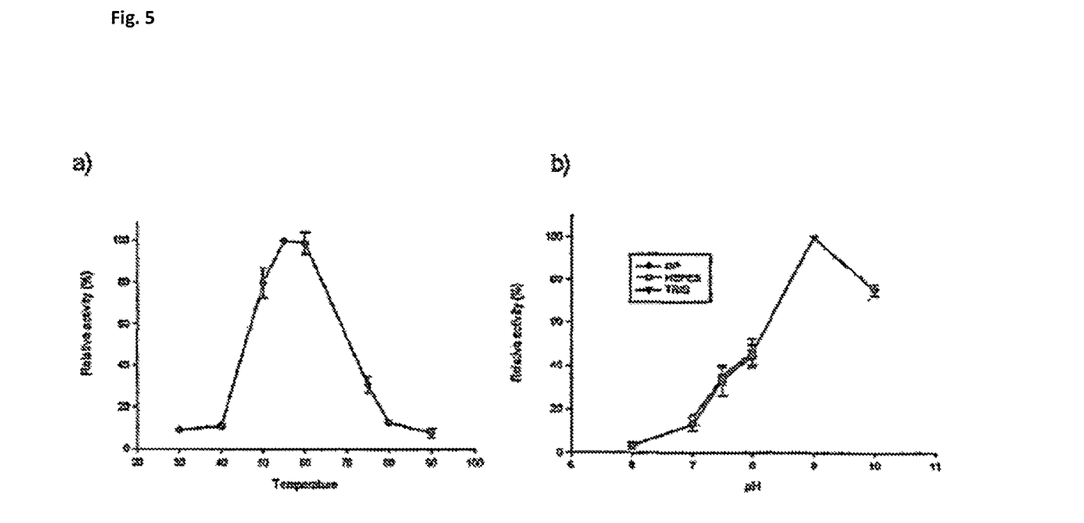
FIG. 5. Methyl ester chromatograms of Ibuprofen and Ibuprofen phenyl ester (methyl ester derivative of the product) (a) and naproxen methyl ester (methyl ester of the derivative of the product) (b) of the corresponding kinetic resolution.

The results of these essays are depicted in FIGS. 2 and 5.

The modified esterase 499EST acted preferably over the phenyl ester enantiomer of ibuprofen, as expected from the photometric detection, using ester of ibuprofen-p-NP with chiral HPLC. It was detected an ee of 40% for the product and 50% for the substrate (phenyl ester of ibuprofen) that leads to an enantioselectivity of E=4 (c=56%) (FIG. 5a). The values were calculated in accordance with the method of Kroutil et al, 1997.

The enzyme showed enantioselectivity of (S) phenyl ester of naproxen. The enantioselectivities towards phenyl naproxen and its p-NP esters were calculated based on the conversions determined by 1H-NMR and the ee of the respective product, also using the same method, as it was described above.

The enantioselectivity of phenyl ester was calculated with E=10 based on a conversion of 52% (1H-RMN) and the ee of naproxen product was of 65% (HPLC) (FIG. 5b). In comparison, the resulting enantioselectivity was 5 times lower for the pNP ester; it was calculated as E=2 based on a conversion of 49% (1H-RMN) and the ee of the naproxen product was of 31% (HPLC).

Thus, the modified enzyme 499EST showed high stereoselectivity in the conversion of the NSAID as the ibuprofen and naproxen. The modified enzyme 499EST was capable of generating (S)-ibuprofen and (S)-naproxen based on racemic samples (FIG. 2).

The invention claimed is:

1. A polynucleotide comprising SEQ ID NO: 1 or encoding an esterase having at least 95% identity with SEQ ID NO:2, wherein said polynucleotide further comprises a 5' sequence encoding a His-Tag and wherein the protein encoded by said polynucleotide has an N-terminal His-tag.

2. A vector comprising the polynucleotide according to claim 1.

3. A host cell transformed with the polynucleotide according to claim 1.

4. The host cell of claim 3, where the cell is *E. coli*.

5. A method for obtaining an enantioselective modified enzyme, comprising the following stages:
   a) inserting a polynucleotide comprising SEQ ID NO: 1 or encoding an esterase having at least 95% identity with SEQ ID NO:2 into a vector;
   b) inserting a polynucleotide encoding a His-Tag at an end of the inserted polynucleotide of step a);
   c) transforming a host cell with the vector;
   d) Over expressing the protein encoded by the polynucleotide in the host cell;
   e) concentrating the host cells and lysing said host cells;
   f) purifying the protein;
   g) concentrating the protein;
   h) storing the protein in buffer at pH 8-10.

6. The method of claim 5, wherein the His-Tag comprises 5-10 residues of histidine.

7. The method of claim 5, wherein the host cell is *E. coli*.

8. The method of claim 5, wherein the purification is made with a chromatographic technique.

9. A method for the production of a protein which comprises culturing the host cell of claim 3 in a suitable medium.

10. An enantioselective modified enzyme with esterase activity comprising a histidine tag encoded by the polynucleotide of claim 1.

11. The enantioselective modified enzyme of claim 10, wherein said enantioselective modified enzyme has an amino acid sequence having a percentage of identity of 97% or higher with the amino acid sequence of SEQ ID NO: 2.

12. The enantioselective modified enzyme of claim 10, wherein said His-Tag comprises 5 to 10 residues of histidine.

13. The enantioselective modified enzyme of claim 12, wherein the His-Tag comprises six residues of histidine.

14. The enantioselective modified enzyme of claim 10, wherein said enantioselective modified enzyme has enantioselective activity at a temperature from 45° C. to 75° C. and pH 6-11.

15. The enantioselective modified enzyme of claim 10, wherein said enantioselective modified enzyme hydrolyzes $C_2$-$C_{12}$ acyl esters.

16. The enantioselective modified enzyme of claim 10, wherein said enantioselective modified enzyme hydrolyzes $C_6$-$C_{10}$ acyl esters.

17. The enantioselective modified enzyme of claim 15, wherein said enantioselective modified enzyme hydrolyzes triacylglycerols.

18. The enantioselective modified enzyme of claim 10, wherein said enantioselective modified enzyme is stable in the presence of DMSO and glycerol.

19. The enantioselective modified enzyme of claim 10, wherein the enzymatic activity of said enantioselective modified enzyme is increased with the addition of $Fe^{+3}$ or Mn.

20. The enantioselective modified enzyme of claim 19, wherein the optimum $Fe^{+3}$ concentration is between 6 and 10 mM.

21. The enantioselective modified enzyme of claim 10, wherein said enantioselective modified enzyme has improved thermo stability in the presence of $Fe^{+3}$.

22. The enantioselective modified enzyme of claim 10, wherein said enantioselective modified enzyme has a selective activity for hydrolysis of (S)enantiomers of racemic mixtures of profen esters.

23. The enantioselective modified enzyme of claim 22, wherein said enantioselective modified enzyme has a selective activity for hydrolysis of (S)enantiomers of racemic mixtures of ibuprofen or naproxen esters.

24. A composition comprising the enantioselective modified enzyme of claim 10 and a preservation agent.

25. The composition of claim 24, further comprising DMSO.

26. The composition of claim 24, further comprising glycerol.

27. A method to prepare optically active (S)-profens, comprising the steps of:
   a) Supplying a racemic mixture of profen esters
   b) Carrying out a dynamic resolution of said racemic mixture of profen esters by reaction of said profen esters with the esterase of claim 10, that has (S)-stereo selectivity in the presence of an organic solvent and a base at a temperature of 45 to 75° C., in which said esterase cleaves the (S)-ester bond of (S)-profen esters of said racemic mixture, and said base promotes the rapid simultaneous racemization of (R)-ester and (S)-ester, and
   c) wherein said reaction has a conversion yield higher than 50% of said profen to said ester(S).

* * * * *